March 25, 1947. C. MALLERIN Plant Pat. 730
ROSE PLANT
Filed Jan. 25, 1944
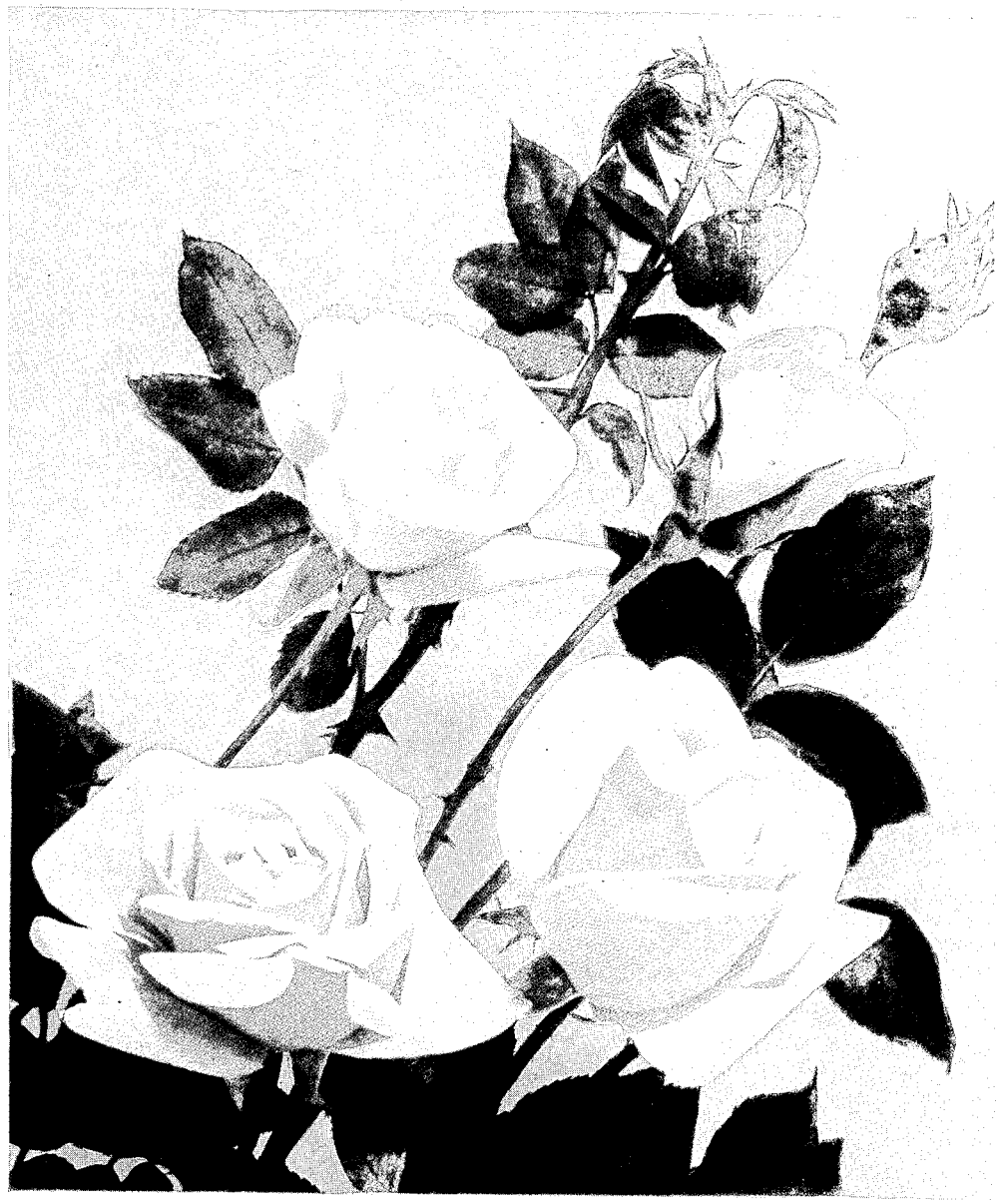
Inventor
Charles Mallerin
By Robb & Robb
Attorneys Patented Mar. 25, 1947

Plant Pat. 730

UNITED STATES PATENT OFFICE

730

ROSE PLANT

Charles Mallerin, Varces, France, assignor to The Conard-Pyle Company, West Grove, Pa., a corporation of Pennsylvania Application January 25, 1944, Serial No. 519,694

1 Claim. (Cl. 47—61)

The present invention appertains to a new and distinct variety of hybrid tea rose plant constituting a marked improvement in its extraordinary and heretofore unmatched qualities in roses of its class.

The new variety results from a cross of "Mme. Arthaud" and an unnamed seedling, by means of which the low vigor and slight fragrance of its seed parent have been changed into a plant of great vigor and strong fragrance.

This new rose is further characterized as to novelty by its long streamlined buds which open into large flowers of 5½ inches diameter and of Coral to Coppery Pink color that not only persist but repeat abundantly on upright, vigorous and shrubby plants.

Asexual reproduction of this new variety shows the foregoing characteristics come true to form and are established.

The following is a detail description of the new variety, color terminology being in accord with Ridgway's Color Standard:

Type: Hardy; bush; outdoor; seedling; for cut flowers and garden decoration.
Class: Hybrid tea.
Breeding: Seedling.
*Seed parent.*—"Mme. Arthaud."
*Pollen parent.*—Unnamed seedling.
Propagation: Holds its distinguishing characteristics through succeeding propagations by budding, which is the only method employed up to the present time.

*Flower*

Locality where grown: West Grove, Pennsylvania.
Flowers borne: Singly and three to stem; on strong, long stems.
Quantity of bloom: Abundant; outdoors.
Continuity: Almost continuous.
Fragrance: Strong; spicy.
Bud:
*Peduncle.*—Medium long; medium heavy; erect; stiff; Mahogany Red, Plate II; numerous prickles.
*Before calyx breaks.*—Size—large. Form—ovoid with conspicuous neck; with foliaceous appendages on the surface of the bud; with bristle-like foliaceous parts extending beyond the tip of the bud equal to one-fourth of its length.

*As calyx breaks.*—Brazil Red, Plate I.
*As first petal opens.*—Size—large. Form—ovoid. Color—outside: Jasper Pink, Plate XIII, washed Light Coral Red, Plate XIII; inside: Salmon Color, Plate XIV, veiled Jasper Pink, Plate XIII.
*Opening.*—Opens up well.
Bloom:
*Size.*—When fully open—large; 4½ inches to 5½ inches.
*Petalage.*—Very double; from 40 to 50 petals; arranged regularly.
*Form.*—Cupped, full high center; becoming high centered; petals remaining tightly rolled outward; becoming later, at maturity, loosely rolled outward.
Petals: Thick; with inside and outside satiny.
*Shape.*—Outside — ovate. Intermediate—ovate. Inside—ovate.

This description of a newly opened flower was made from a rose grown outdoors, in the month of October 1943, at West Grove, Pennsylvania:

*Color.*—*Outside petal*—outside surface: Jasper Pink, Plate XIII, washed Light Coral Red, Plate XIII; inside surface—Salmon Color, Plate XIII. *Intermediate petal*—outside surface: Jasper Pink, Plate XIII, washed Light Coral Red, Plate XIII; inside surface: Salmon Color, Plate XIII. *Inner petal*—outside surface: Ochraceous Salmon, Plate XV; inside surface: Zinc Orange, Plate XV.

This description was made from a rose that was open for three days outdoors, in the month of October, 1943, at West Grove, Pennsylvania:

*Color.*—*Outside petal*—outside surface: Flesh Color, Plate XIV; inside surface: Pale Flesh Color, Plate XIV. *Inside petal*—outside surface: Apricot Buff, Plate XIV; inside surface: Apricot Orange, Plate XIV.
*General color effect.*—Newly opened flower—Salmon Color, Plate XIV. Three days open—Salmon Buff, Plate XIV.
*Behavior.*—Drop off cleanly.
*Flower longevity.*—On bush in garden—4 to 5 days in October. Cut roses grown outdoors kept at living-room temperatures—4 to 5 days in October.

*Reproductive organs*

Stamens: Many; arranged irregularly with petaloids tucked in calyx.
Filaments: Short; English Red, Plate II; most with anthers.
Anthers: Small; Light Cadmium Yellow, Plate IV.
Pollen: Moderately abundant: Lemon Chrome, Plate IV.
Pistils: Many.
Styles: Medium length; thin; bunched.
Stigma: English Red, Plate II.
Ovaries: All enclosed in calyx.
Hips: Short; ovoid; gourd-shaped; Bice Green, Plate XVII; smooth; walls fleshy.
Sepals: Permanent; moderately long; spear-shaped; recurved.
Seeds: Few; medium large.

*Plant*

Foliage:

*Leaves.*—Compound of 3, 5 and 7 leaflets; abundant; moderately large; heavy; leathery.

*Leaflets.*—Shape—ovoid with apex acute. Base—obtuse. Margin—slightly serrate.

*Color.*—*Mature*—upper surface: Yew Green, Plate XXXI; under surface: Jade Green, Plate XXXI. *Young*—upper surface: Morocco Red, Plate I, flushed Olive Green, Plate IV; under surface: Morocco Red, Plate I.

*Rachis (the supporting stem of the compound leaf).*—Medium heavy. Upper side: smooth; grooved. Under side: moderately thorny.

*Stipules.*—Medium length; medium wide; medium long points, turning out at an angle of more than 45°, recurved toward the stem.

*Disease.*—Unusually resistant to mildew and blackspot.

Growth:

*Habit.*—Bushy; upright; much branched.

*Growth.*—Very vigorous.

*Canes.*—Heavy.

*Main stems.*—Dull; Jade Green, Plate XXXI. *Thorns*—several; short; hooked downward; with broad base. *Prickles*—several; Light Cress Green, Plate XXXI. *Hairs*—none.

*Branches.*—Dull; Jade Green, Plate XXXI. *Thorns*—several; short; hooked downward; with broad base. *Prickles*—none. *Hairs*—none.

*New shoots.*—Oxblood Red, Plate I; bright. *Thorns*—many; short; straight; with broad base. *Prickles*—many; Oxblood Red, Plate I. *Hairs*—none.

I claim:

A new and distinct variety of hybrid tea rose plant, characterized as to novelty by its upright, vigorous and shrubby growth bearing flowers opening from long, streamlined buds into large blooms of Coral to Coppery Pink color marked by their persistence and abundance throughout the blooming period, especially in outdoor growing, substantially as shown and described.

CHARLES MALLERIN.